United States Patent [19]
Tomic et al.

[11] Patent Number: 5,360,052
[45] Date of Patent: Nov. 1, 1994

[54] CASTING RING FORMERS

[76] Inventors: Aleksander Tomic, Dvori 9, 66310 Izola, Yugoslavia; Stefan Zaiaznik, Saskova 6, 61201 Ljubljana, Yugoslavia

[21] Appl. No.: 982,247

[22] Filed: Nov. 25, 1992

Related U.S. Application Data

[63] Continuation of Ser. No. 895,888, Jun. 8, 1992, abandoned.

[51] Int. Cl.⁵ ............... B22C 9/04; B22C 7/02
[52] U.S. Cl. ............... 164/412; 164/DIG. 4
[58] Field of Search ............... 164/356, DIG. 4, 6, 164/45, 15, 237, 238, 374, 376, 383, 384, 385, 386, 387; 249/54, 61, 62

[56] References Cited

U.S. PATENT DOCUMENTS

| | | | |
|---|---|---|---|
| 3,196,777 | 7/1965 | Luker | 249/61 |
| 4,777,996 | 10/1988 | Finelt | 164/237 |
| 4,825,934 | 5/1989 | Kai | 249/62 |
| 5,183,095 | 2/1993 | Sullivan | 249/61 |

FOREIGN PATENT DOCUMENTS

| | | | |
|---|---|---|---|
| 600592 | 7/1934 | Germany | 164/376 |
| 2554070 | 6/1977 | Germany | 164/45 |

*Primary Examiner*—P. Austin Bradley
*Assistant Examiner*—Erik R. Puknys
*Attorney, Agent, or Firm*—Herbert Dubno

[57] ABSTRACT

The subject matter of the invention is a casting ring former for forming molds for dental prosthesis products, such as artificial teeth, dental bridges, etc. The casting ring former according to the invention, which represents an improvement with regard to the casting cuvettes known so far is characterized in that they are removed from the mold prior to heat treatment, solves the given technical problem through the use of a specially formed base which may be provided with two nipple-shaped protuberances and two oppositely lying bulges according to a first variant, or up to three pairs of nipple-shaped protuberances and oppositely lying bulges according to a second variant, where in the base thus formed an undulate tape is placed and removed after the mold has cooled and the mold is taken off the base.

4 Claims, 3 Drawing Sheets

CASTING RING FORMERS

CROSS REFERENCE TO RELATED APPLICATION

This is a continuation in part of Ser. No. 07/895,888 filed Jun. 8, 1992 now abandoned.

FIELD OF THE INVENTION

The subject matter of this invention is a casting ring former, i.e. a cuvette intended for forming molds for dental prosthesis products, such as artificial teeth, dental bridges, and the like. The invention is believed to be in class A 61 C 13/20 of International Patent Classification.

BACKGROUND OF THE INVENTION

The technical problem that has been solved by the presented invention is the production of a casting former intended for forming molds for dental prosthesis products that can be used several times, that is easy to manufacture and that is made of inexpensive and environmentally-friendly material, all while preserving the advantages of the casting cuvette types known so far.

The procedures known so far for making molds for dental prosthesis products such as artificial teeth, dentures, bridges, and the like, are based on the production of a mold from a special filling material into which the alloy for dental prosthesis products is poured. The production of the mold involves special forming, free expansion of the filling material while drying, and heat treatment.

Several procedures have been developed for this purpose and several cuvette types have been used, which do not differ much from each other.

The classical and still most frequently used method is based on the use of a casting cuvette consisting of a cylindrical stainless steel body of various volumes and a rubber base with grooves into which the body is placed. The production procedure consists in first coating the inner wall of the cylindrical body with one to three layers (depending on the size of the body) of asbestos, ceramic or paper tape, which allows free expansion of the filling material during heating, and also compensates for the shrinkage of the metal upon cooling. These cuvettes are still commonly used today, but they have a drawback with respect to the damage caused to the stainless steel body during heat treatment, so that the body can only be used a couple of times, while the material it is made of is expensive. In addition, the asbestos or ceramic tape inserts represent a certain expense, too.

A better method uses a cuvette consisting of a cylinder and a base made of injected plastic material. After it has cooled down the mold is squeezed out of the cylinder and heat treated. The plastic material allows unobstructed expansion of the filling material.

Although better than the former one, this system has its drawbacks too. For example when the cuvette is used several times. It can be used 50 times at the most, whereupon the inner walls of the cylindrical body grow rough and the mold can no longer be squeezed out. The cuvette also needs regular washing and cleaning.

A superstructure to the above system is the use of a magnetic tape to replace the cylindrical part of the cuvette. The use is easier, but at least three sizes or lengths of the expensive magnetic tape are required, and the tape has to be cleaned after each use. Besides, at the spot where the ends of the tape run over each other an edge is formed on the mold, and the mold itself may crack at this spot during heat treatment.

Systems consisting of injected cuvette models are also known, which have the same properties as the above mentioned cuvettes made of plastic material, the difference being that the cuvette with the base is made up of three parts which are formed in such a way that about 20% of the material is saved. Because it is assembled of several parts, this cuvette is more expensive, and the production of the mold takes longer.

The casting cuvettes known so far can therefore be divided into two groups with respective drawbacks:

Casting cuvettes with stainless steel cylinders where the mold is heat-treated together with the cuvette are impractical, because the stainless steel cylinder can only be used for a limited, small number of molds and is accordingly expensive.

The other type of casting cuvettes, which is removed prior to heat treatment of the mold, has, despite its advantage over the first type, still minor deficiencies, such as limited number of applications and higher price.

SUMMARY OF THE INVENTION

The casting ring former according to the invention, which represents an improvement over the casting cuvettes known so far, is characterized in that they are removed from the mold prior to heat treatment, and has solved the given technical problem through the application of a specially formed base with or without two nipple-shaped protuberances and two bulges, or several pairs of nipple-shaped protuberances and bulges, with an undulate tape inserted in the base, this undulate tape being removed after the filling material has become solid, and the mold taken off the base.

BRIEF DESCRIPTION OF THE DRAWING

The above and other objects, features and advantages of the present invention will become more readily apparent from the following description, reference being made to the accompanying drawing in which.

DESCRIPTION

Figure 1:
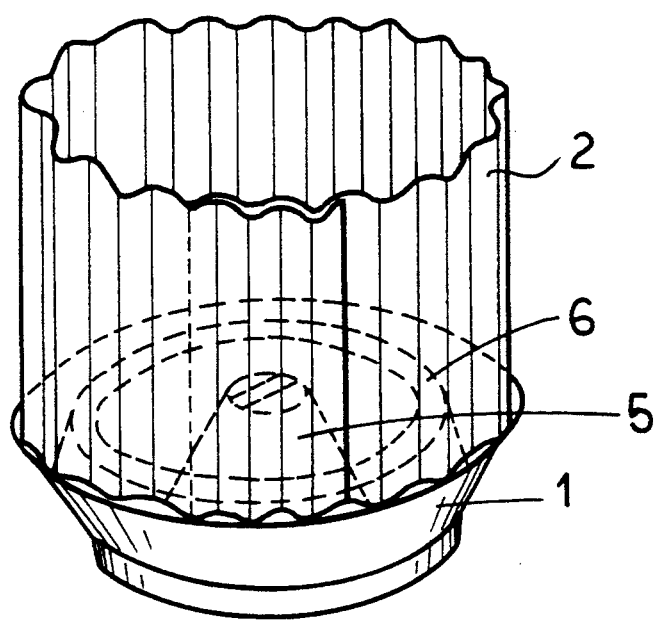
FIG. 1 is a perspective view of the casting ring former according to the invention with an undulate tape inserted in the base.

FIG. 1 shows a casting ring former according to the invention comprising a base 1 and an undulate tape 2 in a perspective view.

The length of the undulate tape 2 agrees with the diameter of the base 1 in such a way that the ends of the undulate tape run over each other by three to four undulations, thus making a cylinder. In specific cases the tape ends covering one another can be additionally fixed by a clamp.

Figure 2:
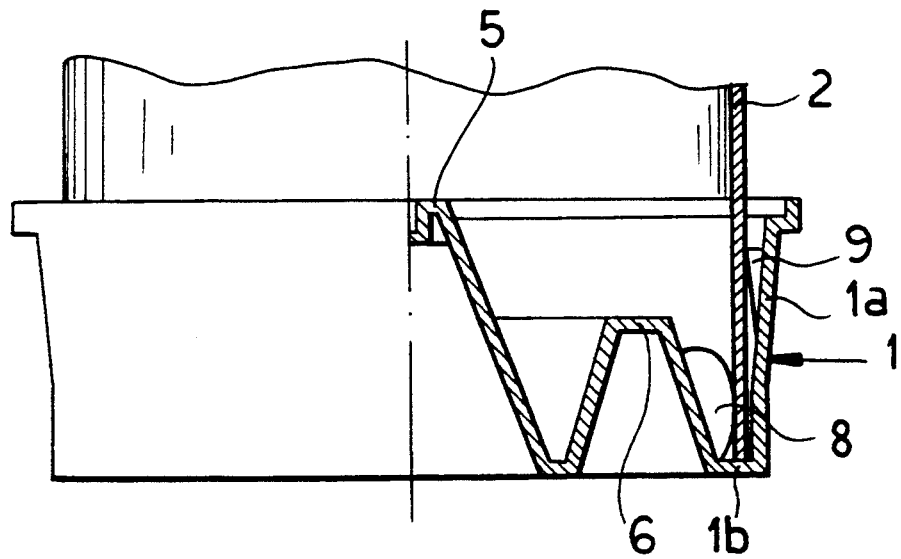
FIG. 2 is a partial cross-section of the casting ring former with an inserted undulate tape according to the invention in side view.
Figure 3:
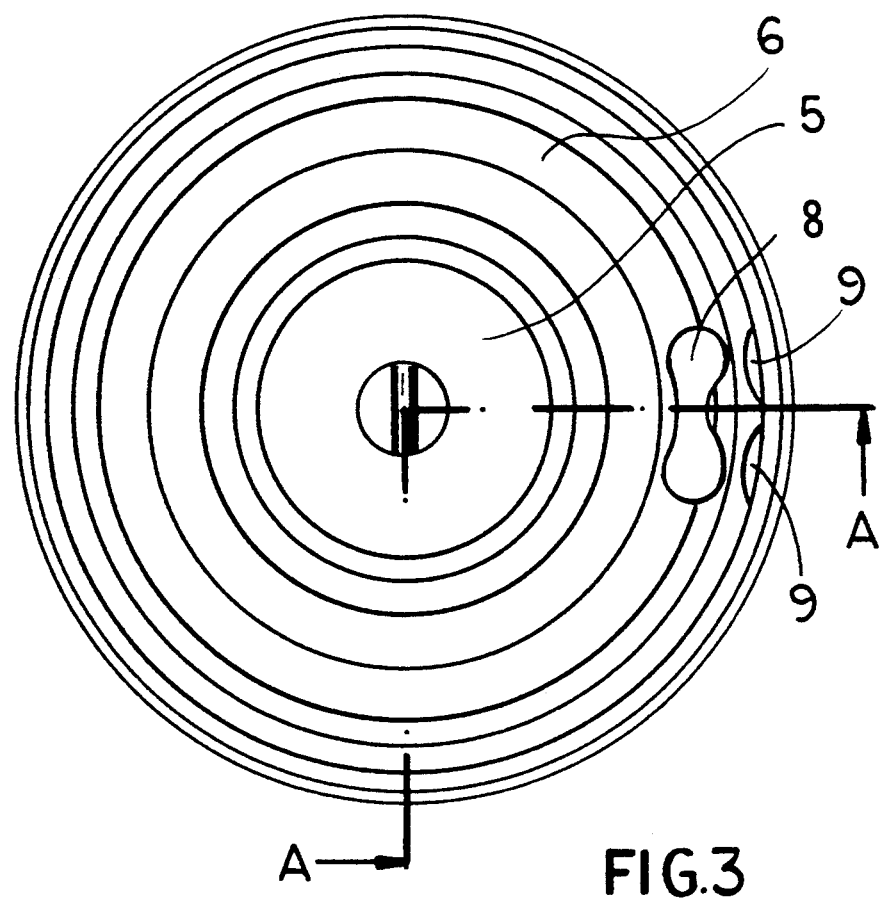
FIG. 3 is a plan view of the casting ring former base according to the invention in a first variant.
Figure 4:
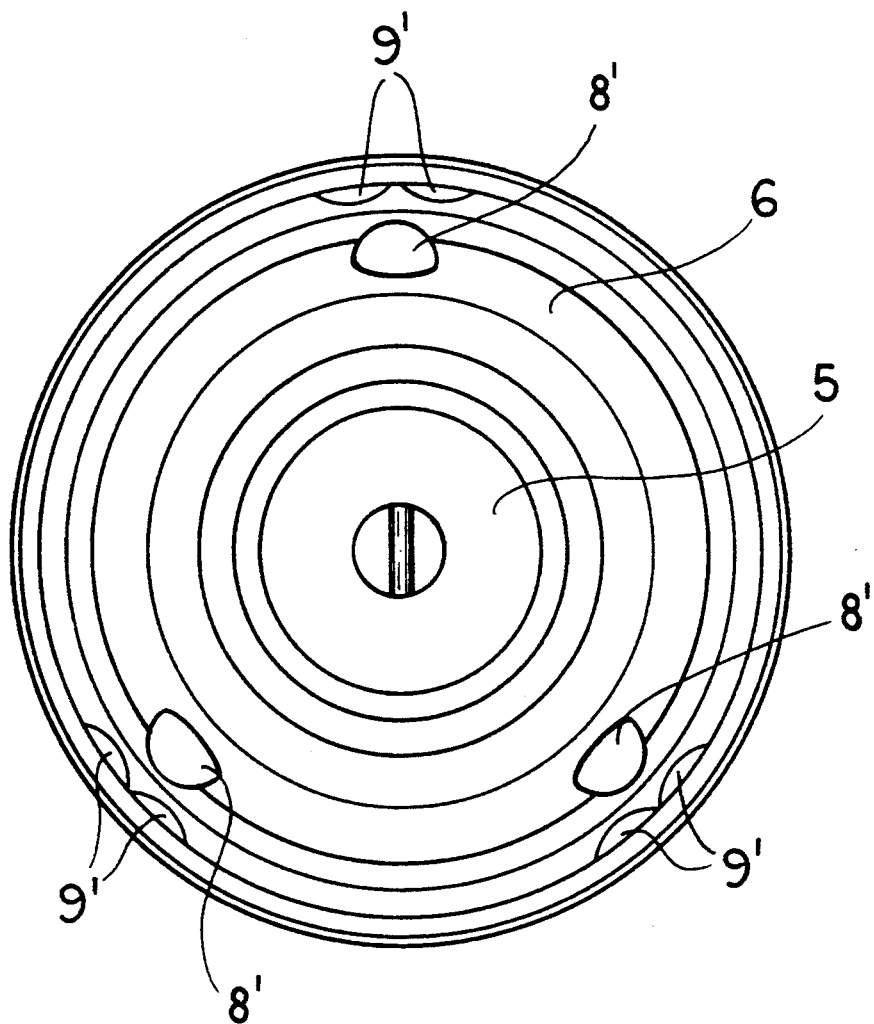
FIG. 4 is a plan view of the casting ring former base according to the invention in a second variant.

A partial cross-section of the assembled casting ring former comprising the base 1 and the undulate tape 2 is shown in FIG. 2.

The base 1 is a cylindrical, shallow cup with a funnel 5 in the middle, onto which the wax positive model of a dental prosthesis product is placed.

The conical outer wall 1a (which has a frustoconical shape—conforming to a frustum of a cone,) of the base 1 enables better fixation or retention of the undulate tape 2. The bottom 1b of the base running towards the funnel 5, makes a thick, cone-shaped edge 5 which, according to a first variant can be fitted with two nipple-shaped protuberances 8 or can be provided without them. When the nipple-shaped protuberances are provided opposite the nipple-shaped protuberances 8, on the wall 1a of the base 1 there are two bulges 9. The combination of nipple-shaped protuberances 8 and bulges 9 provides better fixation and adherence of the undulate tape 2. According to the second variant, the base 1 is fitted with three pairs of nipple-shaped protuberances 8 and bulges 9', in a distance of 120 degrees from one another. The conical-cylindrical shape of the outer wall 1a and that of the walls along the edge 6 make it easier to take the mold off the base 1 after the undulate tape 2 has been removed, and because of the edge 6 less filling material is needed for the production of the mold.

As a result of the undulate tape 2 which, when inserted into the base, forms a cylindrical space which is filled with the filling material, the mold itself takes an undulate shape after the filling material has cooled down and become solid. In this way the area of the mold is increased, and this allows for a more even heating and expansion of the filling material, and a reduction by 20% in the time of heating and cooling. This all means that the heating time is shortened by about an hour, while the cooling takes 15 minutes less and is more evenly distributed. The undulate form of the mold, however, calls for a more careful handling with tongs while transporting the glowing mold from the furnace onto the casting machine.

The advantages of the presented casting ring former over the solutions known so far demonstrate themselves in a smaller volume of the filling material by approximately 25% and increased outer area (thanks to the undulate form) by approximately 28%. The thin and flexible undulate tape permits primary expansion during the cooling of the filling material. The undulate tape can be peeled off the mold, so that the latter is not damaged, and needs no cleaning. The casting ring former (both the base and the undulate tape) is made of less expensive material (by more than 50%) than the casting cuvettes known so far, and the material is environmentally friendly. The greater area of the mold leads to the already mentioned greater area of the mold and, a shorter heating and cooling time.

What is claimed is:

1. A casting ring former for producing a mold for a dental prosthesis, comprising:

a base formed with a central funnel-shaped rise upon which a form for a dental prosthesis can be disposed, and an annular wall surrounding said funnel-shaped rise; and an undulating tape assembly received in said base between said rise and said wall and forming a casting ring in which a material can be cast to provide said mold, said funnel-shaped rise having an upwardly converging frustoconical configuration terminating in a pedestal, said base further comprising a ridge defined between two upwardly converging frustoconical flanks between said rise and said wall, said wall having a frustoconical configuration, an outer one of said flanks is formed with two nipple-shaped protuberances and said wall is formed with two inwardly-extending bulges engageable with said tape for retaining same in a cylindrical configuration within said base.

2. A casting ring former for producing a mold for a dental prosthesis, comprising:

a base formed with a central funnel-shaped rise upon which a form for a dental prosthesis can be disposed, and an annular wall surrounding said funnel-shaped rise; and an undulating tape assembly received in said base between said rise and said wall and forming a casting ring in which a material can be cast to provide said mold, said funnel-shaped rise having an upwardly converging frustoconical configuration terminating in a pedestal, said base further comprising a ridge defined between two upwardly converging frustoconical flanks between said rise and said wall, said wall having a frustoconical configuration, an outer one of said flanks being provided with a plurality of nipple-shaped protuberances angularly equispaced by 120° from one another and said wall is formed with three pairs of bulges each pair being juxtaposed with one of said protuberances for holding said tape within said base in a cylindrical configuration.

3. A casting ring former for producing a mold for a dental prosthesis, comprising:

a base formed with a central funnel-shaped rise upon which a form for a dental prosthesis can be disposed, and an annular wall surrounding said funnel-shaped rise; and an undulating tape assembly received in said base between said rise and said wall and forming a casting ring in which a material can be cast to provide said mold, said rise being provided with a pair of nipple-shaped protuberances confronting said wall and said wall is provided with a pair of bulges juxtaposed with said protuberances and engageable with said tape for holding same in a cylindrical configuration.

4. A casting ring former for producing a mold for a dental prosthesis, comprising:

a base formed with a central funnel-shaped rise upon which a form for a dental prosthesis can be disposed, and an annular wall surrounding said funnel-shaped rise; and an undulating tape assembly with an undulating tape having overlapping ends received in said base between said rise and said wall and forming a casting ring in which a material can be cast to provide said mold said rise being provided along an outer flank thereof with three outwardly-projecting protuberances spaced apart by 120° from one another and said wall is provided with a pair of bulges juxtaposed with each of said protuberances for holding said tape in a cylindrical configuration.

* * * * *

UNITED STATES PATENT AND TRADEMARK OFFICE
CERTIFICATE OF CORRECTION

PATENT NO. : 5,360,052
DATED : Nov. 1, 1994
INVENTOR(S) : Aleksander TOMIC et al It is certified that error appears in the above-identified patent and that said Letters Patent is hereby corrected as shown below:

On the title page, item [76]:

For "Yugoslavia" - each occurrence- read:--Slovenia--

For "Zaiznik" read:  -- ZALAZNIK --

Signed and Sealed this

Eleventh Day of April, 1995

Attest:

BRUCE LEHMAN

*Attesting Officer*     *Commissioner of Patents and Trademarks*